(12) United States Patent
Kaur et al.

(10) Patent No.: US 9,907,758 B2
(45) Date of Patent: Mar. 6, 2018

(54) PROCESS FOR PREPARING SOLID LIPID SUSTAINED RELEASE NANOPARTICLES FOR DELIVERY OF VITAMINS

(71) Applicants: Department of Biotechnology (DBT), New Delhi (IN); University Institute of Pharmaceutical Sciences, Chandigarh, Punjab (IN)

(72) Inventors: Indu Pal Kaur, Chandigarh (IN); Manoj Kumar Verma, Chandigarh (IN)

(73) Assignee: PANJAB UNIVERSITY DEPARTMENT OF BIOTECHNOLOGY (DBT), Punjab (IN)

( * ) Notice: Subject to any disclaimer, the term of this patent is extended or adjusted under 35 U.S.C. 154(b) by 222 days.

(21) Appl. No.: 14/371,338

(22) PCT Filed: Jan. 9, 2013

(86) PCT No.: PCT/IB2013/050169
§ 371 (c)(1),
(2) Date: Jul. 9, 2014

(87) PCT Pub. No.: WO2013/105026
PCT Pub. Date: Jul. 18, 2013

(65) Prior Publication Data
US 2014/0348938 A1 Nov. 27, 2014

(30) Foreign Application Priority Data
Jan. 9, 2012 (IN) .............................. 79/DEL/2012

(51) Int. Cl.
| | | |
|---|---|---|
| *A61K 9/14* | (2006.01) | |
| *A61K 9/51* | (2006.01) | |
| *A61K 9/00* | (2006.01) | |
| *A61K 31/07* | (2006.01) | |
| *A61K 31/122* | (2006.01) | |
| *A61K 31/355* | (2006.01) | |
| *A61K 31/592* | (2006.01) | |
| *A61K 31/593* | (2006.01) | |
| *A61K 31/203* | (2006.01) | |

(52) U.S. Cl.
CPC .......... *A61K 9/5192* (2013.01); *A61K 9/0019* (2013.01); *A61K 9/0053* (2013.01); *A61K 9/5123* (2013.01); *A61K 31/07* (2013.01); *A61K 31/122* (2013.01); *A61K 31/203* (2013.01); *A61K 31/355* (2013.01); *A61K 31/592* (2013.01); *A61K 31/593* (2013.01)

(58) Field of Classification Search
CPC .......... A61K 9/14; A61K 9/141; A61K 9/143; A61K 9/145; A61K 9/146
USPC .................................................. 424/464–500
See application file for complete search history.

(56) References Cited

U.S. PATENT DOCUMENTS

| | | | |
|---|---|---|---|
| 6,814,959 B1 * | 11/2004 | Muller .................... | A61K 8/342 424/400 |
| 2003/0232091 A1 | 12/2003 | Shefer et al. | |
| 2006/0222716 A1 * | 10/2006 | Schwarz ............... | A61K 9/5123 424/489 |
| 2007/0025177 A1 * | 2/2007 | Dahms .................. | B01F 3/0807 366/108 |

FOREIGN PATENT DOCUMENTS

| | | | | |
|---|---|---|---|---|
| EP | 0526666 A1 | 2/1993 | | |
| JP | WO 9420072 A1 * | 9/1994 | ............. | A01N 25/04 |
| WO | WO 94/20072 A1 | 9/1994 | | |
| WO | WO 98/56362 A1 | 12/1998 | | |

OTHER PUBLICATIONS

Castro, G. A. et al. (2007). Development of a new solid lipid nanoparticle formulation containing retinoic acid for topical treatment of acne. *Journal of Microencapsulation*, 24(5), 395-407.
International Search Report, dated May 17, 2013 in connection with PCT International Application No. PCT/IB2013/050169, filed Jan. 9, 2013.

* cited by examiner

*Primary Examiner* — Micah Paul Young
(74) *Attorney, Agent, or Firm* — John P. White; Cooper & Dunham LLP

(57) ABSTRACT

The present invention relates to a simple and convenient process for preparing solid lipid sustained release nanoparticles for delivery of drugs/vitamins, preferably fat soluble vitamins and more specifically Vitamin $D_3$ and retinoic acid (RA). The process involves microemulsion technique. The nanoparticles of Vitamin $D_3$ and RA obtained by the process of the present invention have utility in treatment of diseases like tuberculosis. Use may be extended to other diseases like AMD, diabetic retinopathy, cancers, hyperpigmentation, acne, and osteoporosis.

20 Claims, 10 Drawing Sheets

Figure 10:
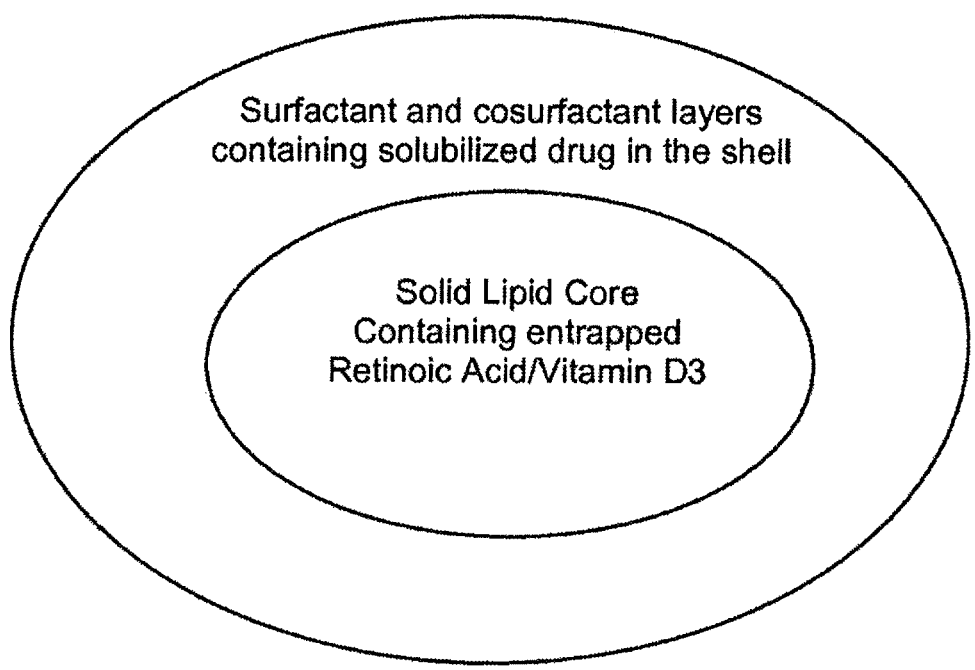

Figure 1: In vitro release study of SLN formulation of ATRA and Vitamin $D_3$
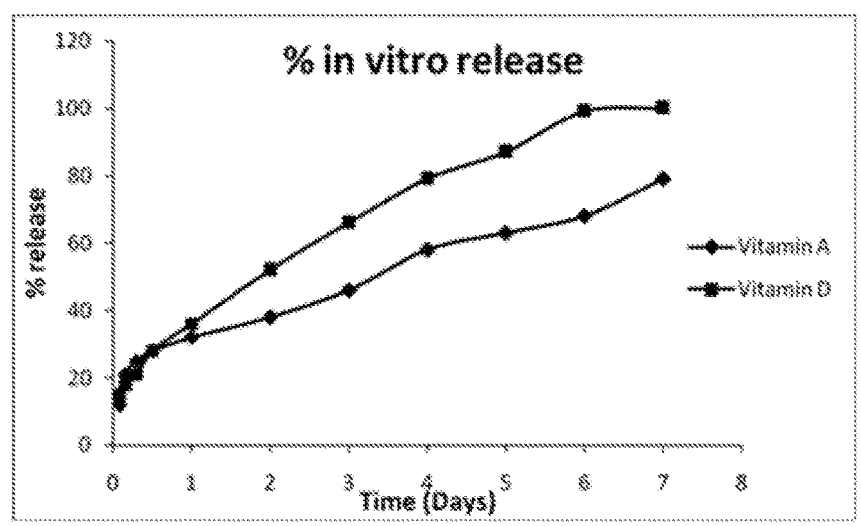

Figure 2: Transmission Electron Microscopy micrograph
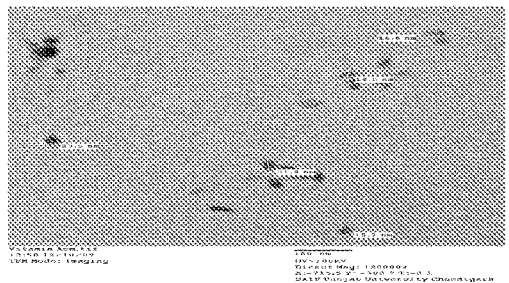 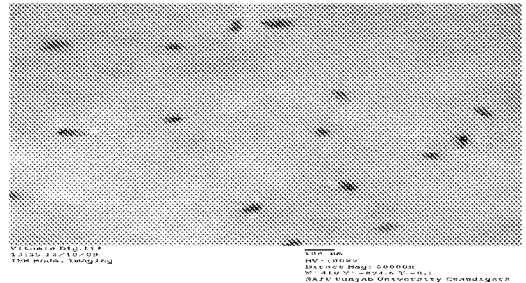
a) ATRA –SLNs     b) Vitamin D$_3$-SLNs

*Figure 3: Differential Scanning Calorimetry (DSC) Data*
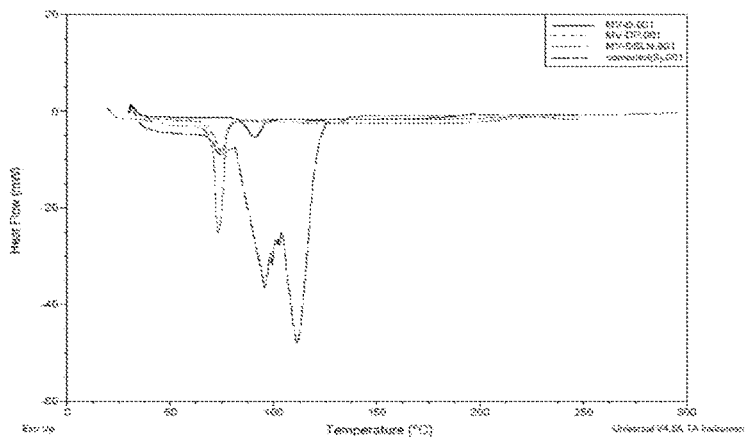
(a) DSC observations of Vitamin $D_3$, Compritol® 888 ATO, Physical mixture of Compritol® 888 ATO and Vitamin $D_3$, and Vitamin $D_3$-SLNs
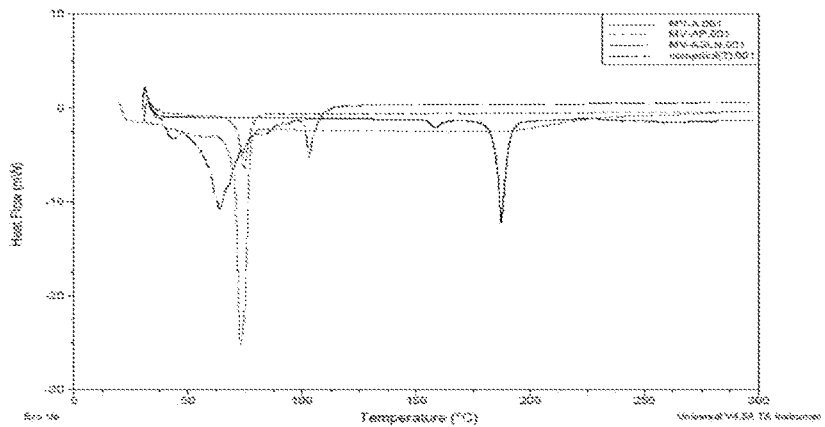
(b) DSC observations of ATRA, Compritol® 888 ATO, Physical mixture of Compritol® 888 ATO and ATRA, and ATRA-SLNs

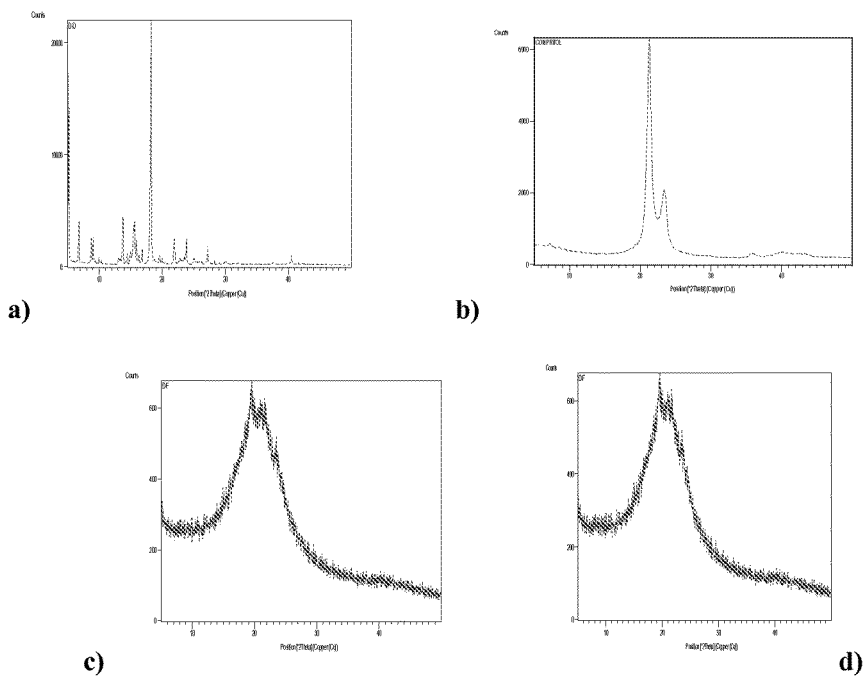
Figure 4: P-XRD OF a) ATRA  b) Compritol 888 ATO  c) Blank (without any drug loading) - SLN  d) ATRA-SLNs.

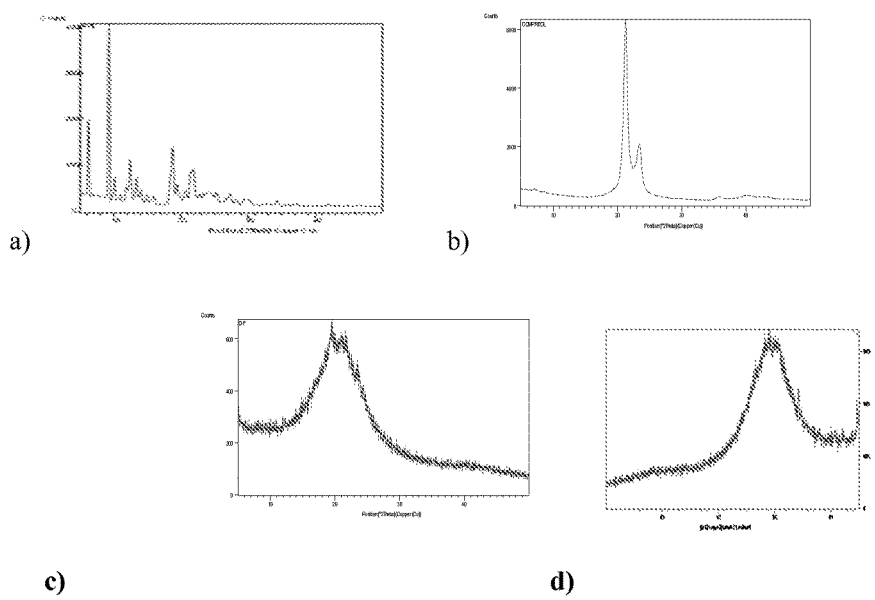
Figure 5: P-XRD OF a) Vitamin D₃ b) Compritol 888 ATO c) Blank (without any drug loading) SLN (d) Vitamin D₃-SLNs

*Figure 6: IR Spectra Analysis*
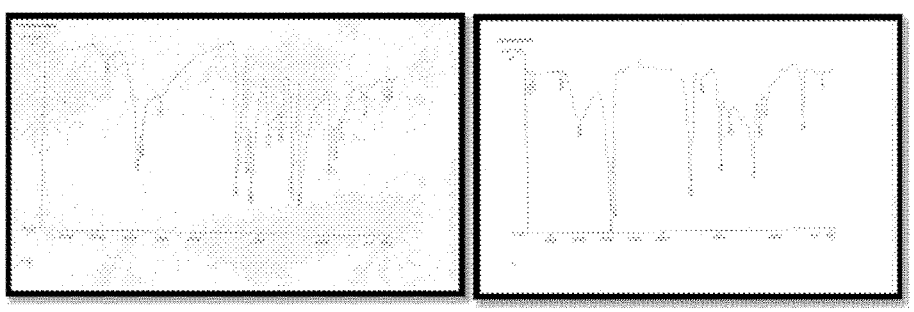
A)					B)
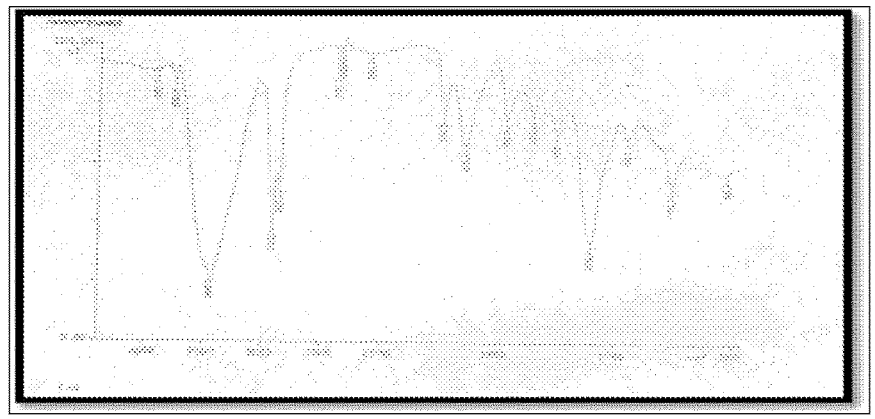
C)
A) IR spectrum of ATRA  B) Compritol 888 ATO  C) ATRA-SLN

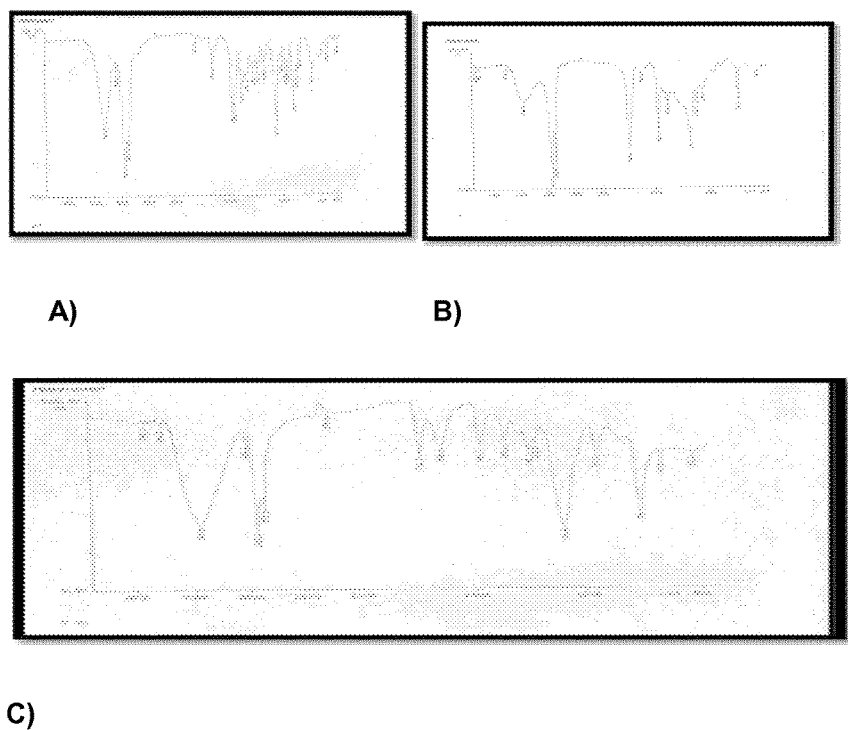
Fig 7 IR spectrum of (A) Vitamin $D_3$ (B) Compritol 888 ATO (C) Vitamin $D_3$-SLN

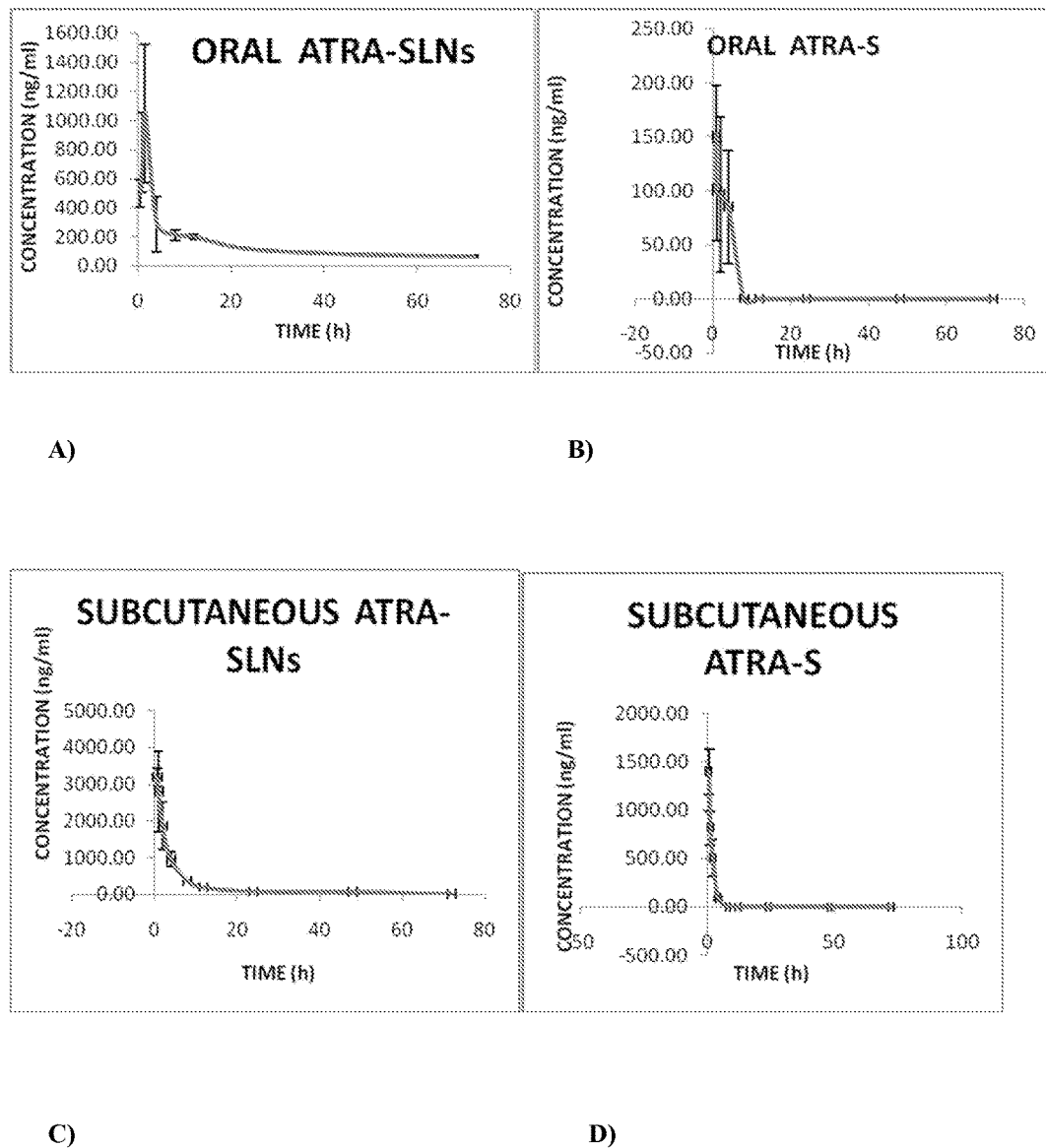
Figure 8: The mean plasma concentration-time curves for different doses of ATRA-SLNs and ATRA-S oral and subcutaneous route of administration.
(A) 1 Lac I.U of oral ATRA-SLNs B) 1 Lac I.U of oral ATRA-S C) 2.5 Lac I.U of subcutaneous ATRA-SLNs D) 2.5 lac I.U of subcutaneous ATRA-S

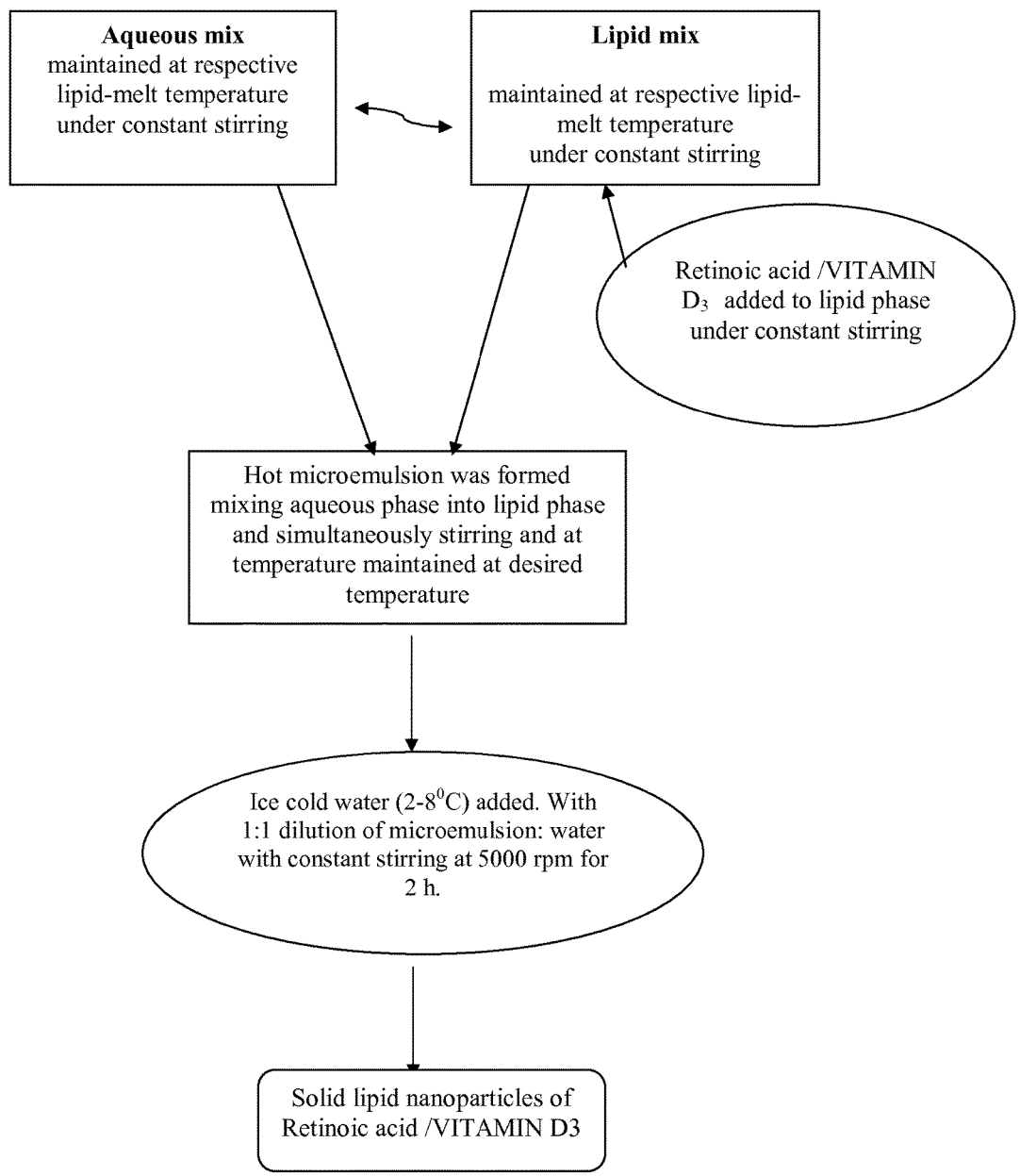
Figure 9: FLOW CHART FOR PREPARATION OF RETINOIC ACID/VITAMIN $D_3$ SOLID LIPID NANOPARTICLES

PROCESS FOR PREPARING SOLID LIPID SUSTAINED RELEASE NANOPARTICLES FOR DELIVERY OF VITAMINS

CROSS-REFERENCE TO RELATED APPLICATIONS

This application is a §371 national stage of PCT International Application No. PCT/IB2013/050169, filed Jan. 9, 2013, claiming priority of Indian Patent Application No. 79/DEL/2012, filed Jan. 9, 2012, the contents of each of which are hereby incorporated by reference in their entirety.

The following specification particularly describes the invention and the manner in which it is to be performed.

FIELD OF THE INVENTION

The present invention broadly lies in the field of nano-biotechnology and particularly relates to the process for preparing solid lipid sustained release nanoparticles for delivery of vitamins, preferably fat soluble vitamins and more specifically Vitamin $D_3$ and retinoic acid (RA). The nanoparticles of Vitamin $D_3$ and Retinoic acid (RA) obtained by the process of the present invention have utility in treatment of diseases like tuberculosis, AMD, diabetic retinopathy, cancers, hyperpigmentation, acne, and osteoporosis.

BACKGROUND & PRIOR ART OF THE INVENTION

The survival of pathogenic mycobacteria is linked to their successful establishment in an intracellular niche within the host. Macrophages have a unique paradoxical role in tuberculosis infection, serving as a first line of defense against such infection and also creating the primary site for mycobacterial replication and dissemination.

Mycobacterial survival within macrophage is achieved primarily by the convolution of mycobacterial phagosome with the endogenous macrophage tryptophan-aspartate-containing coat protein (TACO), also known as coronin-1 that specifically restricts phagosomes containing pathogenic mycobacteria from entering the late endosomal/lysosomal pathway. In fact, this strategy of survival within TACO/coronin-1-coated phagosomes is initiated during the entry itself, and is made possible by the presence of multiple receptors on the phagocyte surface. TACO/coronin-1 is an actin-binding protein known to associate with cholesterol within the plasma membrane. Preference of *Mycobacterium tuberculosis* for cholesterol-rich domains ensures that mycobacteria are sequestered within TACO/coronin-1-coated phagosomes, and therefore evade lysosomal fusion.

Historically, administration of vitamins (A and D) has been considered beneficial for the treatment of tuberculosis it has been shown experimentally that the immunologically active compound retinoic acid (RA) increases the resistance of cultured human macrophages to experimental infection with virulent *M. tuberculosis*. Several studies have also shown the role of vitamin D in tuberculosis wherein TB patients show a low vitamin D status. Retinoic acid and vitamin D are derived from vitamin A and cholesterol respectively. Vitamin $D_3$ and RA act synergistically to activate Vitamin D response and retinoid-X-receptor transcription factor (RXR-TF) that down-regulates TACO gene expression. Thus Vitamin $D_3$+RA synergistically inhibit *mycobacterium* entry as well as survival within macrophages, possibly through rescue of phagosome maturation arrest.

U.S. Pat. No. 5,785,976 discloses solid lipid particles, particles of bioactive agents and methods for the manufacture and use thereof. More specifically the invention is related to the preparation of suspensions of colloidal solid lipid particles (SLPs) of predominantly anisometrical shape with the lipid matrix being in a stable polymorphic modification and of suspensions of micron and submicron particles of bioactive agents (PBAs); as well as to the use of such suspensions or the lyophilizates thereof as delivery systems primarily for the parenteral administration of preferably poorly water-soluble bioactive substances, particularly drugs, and to their use in cosmetic, food and agricultural products.

US Patent Application 20100166865 discloses a method of Nanoparticle-based therapy for a mammalian subject is disclosed. The method uses Nanoparticles and/or Nanoparticles with outer surfaces that contain an affinity moiety effective to bind specifically to a biological surface at which the therapy is aimed, and a hydrophilic polymer coating. The hydrophilic polymer coating is made up of polymer chains either covalently linked or surface adsorbed to the polymer components. After a desired Nanoparticle biodistribution is achieved, the affinity agent binds to the target surface and helps internalize the Nanoparticles. In the above said application the polymeric nanoparticles are prepared, in which polymers and solvents have been used for preparing the same.

U.S. Pat. No. 7,704,986 discloses novel vitamin D analogue which are useful for making pharmaceutical compositions for the prevention or treatment of bone disorders such as osteoporosis.

U.S. Pat. No. 7,153,525 relates to a generalized method of preparation of Solid Lipid Nanoparticles (SLNs) by microemulsion method which discloses a method of making solid nanoparticles, comprising: making an oil-in-water microemulsion by heating, the microemulsion comprising: a liquid nanoparticle matrix material formed by heating a solid matrix material until melted; a surfactant or a co-surfactant or a mixture thereof, and a molecule of interest, wherein the molecule is a drug molecule; wherein the microemulsion is formed essentially spontaneously by heating at a temperature of between about 35° C. and about 100° C.; and cooling the microemulsion while stirring to form solid nanoparticles having a diameter of less than about 300 nanometers, wherein said solid nanoparticles are formed by cooling the microemulsion without aqueous dilution, and where the molecule of interest is either entrapped in or adsorbed to the solid nanoparticles.

Errico et al. published a research article in Int. J. Mol. Sci. 2009, 10(5), 2336-2347; describing a "Colloidal-Coating" based method for the preparation of Retinoic Acid-Loaded Nanoparticles. The method has been developed for the preparation of nanoparticles based on a copolymer of maleic anhydride and butyl vinyl ether (VAM41) loaded with RA and is usable for topical treatment of acne.

Castro G A et al. published a research article in J Microencapsul. 2007 August; 24(5):395-407; describing solid lipid nanoparticles containing all-trans retinoic acid (RA) for topical treatment of acne. Different formulations were prepared using glyceryl behenate as lipid matrix. The aim of this work was to develop SLN using a low surfactant/lipid ratio.

Li Q et al. published a research article in J Agric Food Chem. 2011 Mar. 9; 59(5):1962-7. describing preparation and characterization of nanoparticles based on hydrophobic alginate derivative as carriers for sustained release of vitamin $D_3$.

Almouazen et al. published a research article in Pharm Res (2012) describing polymeric nanoparticles of Calcitriol (1,25-dihydroxyvitamin D(3), the active metabolite of vitamin D(3).

SLNs combine the advantages of lipid emulsion and polymeric nanoparticle systems while overcoming the temporal and in vivo stability issues that troubles the conventional as well as polymeric nanoparticles drug delivery approaches. SLNs combine numerous advantages over the other colloidal carriers i.e. incorporation of lipophilic and hydrophilic drugs feasible, no biotoxicity of the carrier, avoidance of organic solvents, possibility of controlled drug release and drug targeting, increased drug stability and no problems with respect to large scale production. Advantages of SLNs are the use of physiological lipids, the avoidance of organic solvents, a potential wide application spectrum (dermal, per os, intravenous) and the high pressure homogenization as an established production method. Additionally, improved bioavailability, protection of sensitive drug molecules. SLNs in general have high drug loading capacity, large surface area, small size, more stability than biological liposomes. They are readily biodegradable and less toxic than ceramic or polymer nanoparticles. A clear advantage of SLNs over polymeric nanoparticles is the fact that their matrix is made from physiologically tolerated lipid components, which decreases the potential for acute and chronic toxicity associated with some polymers or the monomers thereof. Further, the method used for their production does not usually involve organic solvents, as the latter have safety concerns.

The nanoparticles produced by the earlier methods known in the prior art have various disadvantages like low entrapment efficiency, an erratic release profile, low loading capacity, low drug stability etc. Moreover the SLNs produced by the earlier processes involved use of stringent conditions, harmful organic solvents, strict modulation and monitoring at different levels.

There is need, therefore, for a simple and convenient process for the preparation of sustained release SLNs for delivery of fat soluble vitamins like vitamin $D_3$ and retinoic acid (RA), which can overcome the drawbacks of the prior art.

Vitamin A and D are photo and air sensitive, water insoluble molecules which are highly prone to oxidation on exposure to air, with a limited bioavailability. SLNs of vitamin A and D can increase their stability, their blood residence time and suitably modify their biodistribution resulting in a sustained release of these molecules especially when administered subcutaneously.

Accordingly, the present invention packages these agents into SLNs so as to maintain a desired therapeutic concentration in plasma for a sufficient period of time such that the infecting *mycobacterium* is flushed out of the system as the vitamin A and D down regulates its anchoring site on macrophages. Such SLNs encapsulate the drug in a protected solid matrix so as to prevent their degradation, and improve the stability.

The process of the present invention is a simple and convenient process, involving less stringent conditions and avoids the use of biologically intolerable solvents. SLNs of the present invention are highly effective in sustained release delivery of Vitamins, especially fat soluble vitamins like Vitamin $D_3$ and Retinoic Acid. Moreover, the SLNs of the present invention have several other covert advantages, for delivery of vitamins, which include high entrapment efficiency, increased in-vivo stability and sustained release over an extended period of time. The novelty of present invention is also reflected in the production of concentrated formulation of SLNs with a least dilution of 1:1 which has never been reported in literature till date. Also no data on preparation and evaluation of Vitamin A and Vitamin D loaded solid lipid nanoparticles for oral/subcutaneous route of drug administration exists in the public domain. The process of the present invention has never been disclosed in the literature, more particularly for these particular drugs i.e Vitamin A and Vitamin D. The present invention for the first time reports SLNs comprising of vitamin $D_3$ and Retinoic acid (RA) for treatment of tuberculosis, an indication unreported earlier.

Objects:

Some of the objects of the present disclosure are as follows:

It is an object of the present disclosure to provide a simple and convenient process for preparing solid lipid nanoparticles.

It is an object of the present disclosure to provide a process for preparing solid lipid nanoparticles involving micro-emulsification method.

It is another object of the present disclosure to provide solid lipid nanoparticles.

It is still another object of the present disclosure to provide sustained release solid lipid nanoparticles.

It is still another object of the present disclosure to provide solid lipid nanoparticles having improved entrapment efficiency.

It is still another object of the present disclosure to provide solid lipid nanoparticles with improved entrapment efficiency and sustained release of fat soluble vitamins like Vitamin A and Vitamin D.

It is still further object of the present disclosure to provide solid lipid nanoparticles which reduce the dosing frequency and dose dependent side effects.

It is yet another object of the present disclosure to provide a concentrated formulation of solid lipid nanoparticles, wherein the ratio of microemulsion and water ranges between 1:1 to 1:4.9.

SUMMARY

In one aspect of the present disclosure there is provided a process for preparing solid lipid nanoparticles, said process comprising the following steps:

i) preparing a lipid mix by melting at least one lipid selected from the group consisting of glycerides and fatty acids;

ii) preparing an aqueous emulsifier mix by admixing at least one emulsifier and water followed by heating at a temperature at least equal to the melting point of the selected lipid of step (i) and maintaining the said temperature for desired time interval;

iii) adding at least one vitamin to the lipid or lipid mix to obtain a solution or dispersion;

iv) mixing the lipid mix of step (iii) with the aqueous emulsifier mix of step (ii) to obtain a hot microemulsion;

v) stirring the hot microemulsion of step (iv) and simultaneously maintaining the temperature at the temperature of the lipid mix;

vi) adding microemulsion of the step (v) to the ice cold water in 1:1 ratio;

vii) stirring the mixture of step (vi) at 5000 rpm for 1.5 to 3 hours; and
viii) obtaining an aqueous dispersion of solid lipid nanoparticles having a particle size in the range of 5 nm to 500 nm, preferably 5 nm to 250 nm.

The present invention also provides SLNs comprising of vitamin $D_3$ and Retinoic acid (RA) for treatment of tuberculosis.

The solid lipid nanoparticles are provided, wherein the particle size of the solid lipid nanoparticles ranges between 5 nm to 500 nm, preferably between 5 nm to 250 nm.

The amount of vitamin in solid lipid nanoparticles is in the range of about 5 to about 40% with respect to the mass of the lipid.

The entrapment of the vitamins was found in the range of 60% to 100%.

The present invention also provides a concentrated nanoformulation, wherein the ratio of microemulsion and water ranges between 1:1 to 1:4.9.

BRIEF DESCRIPTION OF ACCOMPANYING DRAWING

The accompanying drawings illustrate embodiments of the invention and, together with the description, serve to explain the invention. These drawings are offered by way of illustration and not by way of limitation.

FIG. 1 illustrates in vitro release study of SLN formulation of ATRA and Vitamin $D_3$; In vitro release study of SLN formulation of ATRA (Vitamin A) and Vitamin $D_3$ was performed using 0.01M Phosphate Buffer pH 7.4 as the release media maintaining temperature at 37° C. and speed at 50 rpm. For vitamin A, 79% release was obtained up to 7 days and 100% release was obtained for vitamin D after 7 days.

FIG. 2 illustrates Transmission Electron Microscopy micrograph of a) ATRA-SLNs b) Vitamin $D_3$-SLNs FIG. 3 (a) illustrates Differential Scanning Calorimetry (DSC) Data; DSC observations of Vitamin $D_3$, Compritol® 888 ATO, Physical mixture of Compritol® 888 ATO and Vitamin $D_3$, and Vitamin $D_3$-SLNs (b) DSC observations of ATRA, Compritol® 888 ATO, Physical mixture of Compritol® 888 ATO and ATRA, and ATRA-SLNs FIG. 4 illustrates P-XRD of a) ATRA, b) Compritol 888 ATO, c) B-SLN, d) ATRA-SLNs.

FIG. 5 illustrates P-XRD of a) Vitamin $D_3$, b) Compritol 888 ATO, c) Blank SLN, (d) Vitamin $D_3$-SLNs FIG. 6 illustrates IR Spectra Analysis Data; IR spectrum of A) ATRA, B) Compritol 888 ATO, C) ATRA-SLN FIG. 7 illustrates IR Spectra Analysis Data IR spectrum of (A) Vitamin $D_3$, (B) Compritol 888 ATO, (C) Vitamin $D_3$-SLN FIG. 8 illustrates the mean plasma concentration-time curves for different doses of ATRA-SLNs and ATRA-S oral and subcutaneous route of administration; (A) 1 Lac I.U of oral ATRA-SLNs, B) 1 Lac I.U of oral ATRA-S, C) 2.5 Lac I.U of subcutaneous ATRA-SLNs, D) 2.5 lac I.U of subcutaneous ATRA-S FIG. 9 depicts Flow Chart for preparation of Retinoic Acid/Vitamin $D_3$ Solid Lipid Nanoparticles FIG. 10 illustrates the general structure of the SLNs of the invention.

DETAILED DESCRIPTION OF THE INVENTION

The present invention is described with reference to the tables/figures etc. and specific embodiments; this description is not meant to be construed in a limiting sense. Various alternate embodiments of the invention will become apparent to persons skilled in the art, upon reference to the description of the invention. It is therefore contemplated that such alternative embodiments form part of the present invention.

Unless defined otherwise, technical and scientific terms used herein have the same meaning as commonly understood by one of ordinary skill in the art to which this invention belongs.

Accordingly, the present invention relates to a simple and convenient process for the preparation of sustained release nanoparticles for delivery of fat soluble vitamins like vitamin $D_3$ and retinoic acid (RA). The SLNs of vitamin $D_3$ and Retinoic acid (RA) obtained by the process of the present invention have their utility in treatment of tuberculosis.

It is proposed that SLNs of Vitamin A and D administered orally/subcutaneously will achieve a controlled and sustained release so as to maintain their desired and prolonged therapeutic concentration in plasma for at least 4-7 days. Later may be achieved by a daily or less frequent dosing. The hypothesis is that the normal life cycle of *M. tuberculosis* is 5-7 days and once it is unable to establish itself on the macrophages it will die and will be flushed out from the system.

SLNs of both Vitamin $D_3$ and Vitamin A have been produced by the process of the present invention.

SLNs possess a solid lipid core matrix that can solubilize lipophilic molecules. The lipid core is stabilized by surfactants (emulsifiers). The lipids in general include triglycerides (e.g. tristearin), diglycerides (e.g. glycerol bahenate), monoglycerides (e.g. glycerol monostearate), fatty acids (e.g. stearic acid), steroids (e.g. cholesterol), and waxes (e.g. cetyl palmitate). All classes of emulsifiers (with respect to charge and molecular weight) can be used to stabilize the lipid dispersion.

Typically, the glyceride of the present invention is at least one selected from the group consisting of mono-glycerides, di-glycerides and tri-glycerides.

In accordance with one of the embodiments of the present disclosure the glyceride is at least one selected from the group consisting of glyceryl behenate, tricaprin, trilaurin, trimyristin, tripalmitin, tristearin, 1,2-dioctanoyl-sn-glycerol, 1,2-didecanoyl-sn-glycerol, 1,2-dilauroyl-sn-glycerol, 1,2-dimyristoyl-sn-glycerol, 1,2-dipalmitoyl-sn-glycerol, 1-palmitoyl-2-oleoyl-sn-glycerol, 1-stearoyl-2-linoleoyl-sn-glycerol, 1-stearoyl-2-arachidonoyl-sn-glycerol, 1-stearoyl-2-docosahexaenoyl-sn-glycerol, 1-oleoyl-2-acetyl-sn-glycerol, 1,2-di-O-phytanyl-sn-glycerol, 1,2-dipalmitoyl ethylene glycol, 1-2-dioleoyl ethylene glycol, glyceryl monostearate, behenoyl polyoxyl-8 glycerides, glyceryl palmitostearate, 1-O-hexadecyl-sn-glycerol, 1-O-hexadecyl-2-acetyl-sn-glycerol, 1-O-hexadecyl-2-O-methyl-sn-glycerol, 1,2-diacyl-3-O-(α-D-glucopyranosyl)-sn-glycerol, stearoyl macrogol-32 glycerides, stearoyl polyoxyl-32 glycerides, lauroyl macrogol-32 glycerides, lauroyl polyoxyl-32 glycerides, lauroyl macrogol-6 glycerides, lauroyl polyoxyl-6 glycerides, oleoyl macrogol-6 glycerides, oleoyl polyoxyl-6 glycerides, linoleoyl macrogol-6 glycerides, polyglyceryl-3 dioleate, glycerol monolinoleate, glyceryl monolinoleate, glycerol monooleates, diethylene glycol monoethyl ether, glyceryl dibehenate, glycerol distearate, glyceryl distearate, glyceryl dipalmitostearate and linoleoyl polyoxyl-6 glyceride. Preferably, the glyceride is Glyceryl dibehenate EP or Glyceryl behenate NF/CR.P i.e. Compritol 888ATO.

Typically, the fatty acid is selected from the group consisting of saturated C4-C28 fatty acids and unsaturated C4-C28 fatty acids. Preferably, the fatty acid is stearic acid.

Typically, the emulsifier is at least one selected from the group consisting of anionic emulsifiers, cationic emulsifiers, non ionic emulsifiers or zwitterionic emulsifiers. In accordance with one of the embodiment of the present disclosure the emulsifier is at least one selected from the group consisting of soy lecithin, egg lecithin, phosphatidylcholine; ethylene oxide copolymers, propylene oxide copolymers, poloxamers, sorbitan ethylene oxide/propylene oxide copolymers, polysorbate 20, polysorbate 60, polysorbate 80, sorbitan esters, span 20, span 40, span 60, span 80, alkyllaryl polyether alcohol polymers, tyloxapol, bile salts, cholate, glycocholate, taurocholate, taurodeoxycholate, gemini surfactants and alcohols. Preferably, the emulsifiers are Polysorbate 80 and Soya Lecithin.

Typically, the drug/vitamins are selected from fat soluble vitamins like Vitamins A, D, E and K. Preferably, the Vitamins are Vitamins A and its other forms like (Retinoic acid, Vitamin A Retinol, retinal, and four carotenoids including beta carotene, ATRA, or its derivatives or other metabolites) and Vitamin D and its other forms like [cholecalciferol (Vitamin $D_3$) or ergocalciferol (Vitamin $D_2$) or its derivatives or other metabolites].

The present invention provides a process for preparing SLNs, said process comprising the following steps:
i) preparing a lipid mix by melting at least one lipid selected from the group consisting of glycerides and fatty acids;
ii) preparing an aqueous emulsifier mix by admixing at least one emulsifier and water followed by heating at a temperature at least equal to the melting point of the selected lipid of step (i) and maintaining the said temperature for desired time interval;
iii) adding at least one vitamin to the lipid or lipid mix to obtain a solution or dispersion;
iv) mixing the lipid mix of step (iii) with the aqueous emulsifier mix of step (ii) to obtain a hot microemulsion;
v) stirring the hot microemulsion of step (iv) and simultaneously maintaining the temperature at the temperature of the lipid mix;
vi) adding microemulsion of step (v) to ice cold water in 1:1 ratio;
vii) stirring the mixture of step (vi) at 5000 rpm for 1.5 to 3 hours; and
viii) obtaining an aqueous dispersion of solid lipid nanoparticles having a particle size in the range of 5 nm to 500 nm, preferably 5 nm to 250 nm.

The process of the invention alternatively involves preparing an aqueous emulsifier mix comprises mixing more than one emulsifiers. The selected emulsifiers could also serve as surfactants.

The process of the invention involves the step of dispersing the microemulsion in water maintained at a temperature ranging between 0° C. and 5° C. under continuous stirring/homogenizing to obtain solid lipid nanoparticles, wherein the ratio of microemulsion and water ranges between 1:1 to 1:4.9.

The process of the invention also involves dispersing the micro emulsion in water by continuous stirring/homogenizing at 4,000 to 12,000 rpm, preferably 5,000 to 7,000 rpm for a time period ranging between 20 minutes and 2 hours.

As another embodiment, the present application also provides SLNs comprising:
i at least one lipid selected from the group consisting of glycerides and fatty acids, such as herein described;
ii at least one vitamin or its alternate form or its derivative, selected from fat soluble vitamin such as Vitamin A, D, E and K; and
iii at least one emulsifier, such as herein described.

The amount of vitamin in SLNs is in the range of about 5 to about 40% with respect to the mass of the lipid.

The particle size of the SLNs ranges between 5 to 500 nm, preferably between 5 to 250 nm.

The entrapment of the vitamins was found in the range of 60% to 100%

As yet another embodiment, the invention provides a concentrated nano-formulation, wherein the ratio of microemulsion and water ranges between 1:1 and 1:1.49

According to yet another embodiment the route of administration of the nano-formulation is selected from a group comprising oral, nasal, topical, and parenteral route of administration.

The SLNs of the present invention have the following structure:
1. Innermost lipid core consisting of a solid lipid encapsulating the drug/vitamin (Retinol/Vitamin $D_3$) in its solid matrix.
2. The shell referred to as the outer layer consist of a mixture of surfactant and co-surfactant and in turn stabilize the inner lipid core.
3. The formed nanoparticulate structure is finally surrounded by the aqueous surfactant solution of unentrapped drug but in the solubilized form.

EXAMPLES

The present disclosure with reference to the accompanying examples describes the present invention. However, those of skill in the art should, in light of the present disclosure, appreciate that many changes can be made in the specific embodiments which are disclosed and still obtain a like or similar result without departing from the spirit and scope of the invention. It is understood that the examples are provided for the purpose of illustrating the invention only, and are not intended to limit the scope of the invention in any way.

Example 1

Materials and Methods
1. Drug Excipients Interaction Studies

Drug excipients interaction studies were done at 4° C., 40° C., 40° C. and 75% RH for 1 month. Selection of lipid was done from a repertoire of lipids such as, glyeryl mono, di, tri, glycerides, stearic acid, glyerylpalmitostearte, glycerylmonostearte, palmitic acid, oleic acid, saturated and unsaturated fatty acids. These lipids were mixed with surfactants, such as tween 20, tween 40, tween 60, tween 80, span 20, span 40, Span 60, poloxamers, PEG (400, 600, 4000, 6000) etc. and co-surfactants blend selected from Phospholipon G, Phospholipon H, egg lecithin, Soy lecithin etc. Purified and sterile water was used all throughout the study.

2. Process for Preparation of SLNs by Microemulsification Method

Optimized formulation comprising of emulsifiers such as Polysorbate 80 (45.45%), soy lecithin (0.58%), and water were placed together in a beaker and heated to the lipid melt temperature. Lipid (7.27%) was melted separately at 82-85° C. Drug (Retinoic acid/vitamin $D_3$) was added to the Lipid phase, following which the hot aqueous emulsifier mix, was dropped at once into the lipid melt, under magnetic stirring to obtain a clear microemulsion. The hot microemulsion thus formed, was transferred into an equivalent amount of cold water (−2° C.) under continuous mechanical stirring (5000 rpm) for 2 h. In the aqueous medium, SLNs are formed by crystallization of the oil droplets present in the microemulsion. The prepared SLNs were stored in a refrigerator until further analysis.

3. Physicochemical Characterization of SLNs

The physicochemical characterization of SLNs were done using techniques such as Total drug content, Drug entrapment, Entrapment efficiency, Particle Size Analysis, Transmission Electron Microscopy (TEM) analysis, Differential Scanning Calorimetry (DSC) studies, IR Spectra Analysis, In vitro release, Stability studies, Pharmacokinetic, studies and the like as discussed below.

4. Total Drug Content:

1 ml of the SLN dispersion was taken and disrupted using an appropriate volume of chloroform:methanol (1:1) till a clear solution was obtained. The absorbance of the clear solution thus obtained was measured at $\lambda_{max}$ of 351 nm for Retinoic acid and $\lambda_{max}$ of 265 nm for vitamin $D_3$ and the total drug content was then calculated in the prepared dispersion using the dilution factor.

5. Entrapment Efficiency:

For determining the entrapment efficiency, SLN dispersion was ultracentrifuged at 1, 00,000 rpm for 2 h at 4° C. The clear supernatant was decanted. The pellet of SLNs was than washed with methanol to remove the unentrapped drug. The two supernatants were combined and the absorbance of both the supernatant and the pellet disrupted and dissolved in a suitable solvent was recorded after appropriate dilutions. Absorbance value obtained for blank Nano-colloidal lipidic particles treated in a similar manner was used as the control value to compensate for any interference of the ingredients. All the determinations were performed in triplicate. Methanol:chloroform (1:1, v/v) was used to dissolve the pellets of nano-colloidal lipidic particles. Amount of drug in the pellet gave a direct measure of the extent of drug entrapped.

$$\text{Entrapment efficiency} = \frac{\left(\begin{array}{c}\text{Amount of drug/ml of } SLN \text{ dispersion} \times \\ \text{Total volume of dispersion}\end{array}\right)}{\text{Total drug incorporated}} \times 100$$

6. Particle Size Analysis:

The mean diameter of nano-colloidal lipidic particles in the dispersion (with appropriate dilutions using triple distilled water) was determined using laser diffraction (Mastersizer 2000, Malvern Instruments, UK). Appropriate dilutions of the dispersion were made for particle size determination.

7. Transmission Electron Microscopy:

Morphology of Nano-colloidal lipidic particles was examined using an electronic transmission microscope (Hitachi H-100, Japan).

8. Differential Scanning Calorimetry (DSC) Studies:

DSC was performed with a Perkin-Elmer Differential calorimeter. DSC is a tool to investigate the melting and recrystallization behavior of crystalline materials like Nano-colloidal lipidic particles. The breakdown or fusion of the crystal lattice by heating or cooling the sample yields information about the internal polymorphism, crystal ordering, or glass transition processes. It uses the fact that different lipid modifications possess different melting points and enthalpies. The thermal analysis of the pure drug, excipients and SLN were done to observe for any significant changes in the pattern of the peaks.

9. Powder X-Ray Diffraction (PXRD)

The encapsulation of drug inside the nanoparticles was confirmed by X-ray diffraction measurements carried out with an X-ray diffractometer (XPERT-PRO, PANalytical, Netherlands). PXRD studies were performed by exposing the samples to $CuK_\alpha$ radiation (45 kV, 40 mA) and scanning from 5° to 50°, 2θ at a step size of 0.017° and scan step time of 25 s. Samples used for PXRD analysis were same as those of DSC analysis. The instrument measures interlayer spacing d which is calculated from the scattering angle θ, using Bragg's equation $n\lambda = 2d \sin \theta$ where $\lambda$ is the wavelength of the incident X-ray beam and n is the order of the interference. Obtained XRD patterns were compared for characteristic drug peak intensity 10. FTIR Spectra Analysis:

The IR spectroscopy is used to elaborate the structure and stereochemistry of the bulk material and the nanoparticles. Analysis of the drug, lipid, bulk mixture and Nano-colloidal lipidic particles were done. The peaks obtained with the bulk mixture and the lyophilized formulation of Nano-colloidal lipidic particles was compared for any significant changes.

11. In Vitro Release:

Dialysis bag method to study the drug release was performed using (0.01 M Phosphate buffer pH 7.4, (FIG. 1) as the dissolution medium. The dialysis bags (12 kDa, Hi Media) were soaked in de-ionized water for 12 h before use. One milliliter of SLN dispersion was poured into the dialysis bag. The bag was placed in a beaker containing 100 mL dissolution medium maintained at 37±0.5° C. and stirred at a rate of 50 rpm. Aliquots of the dissolution medium were withdrawn at different time intervals and were replaced with the same volume of fresh medium to maintain the sink conditions. The samples were suitably diluted and analyzed for Retinoic acid and vitamin $D_3$. All the operations were carried out in triplicate.

12. Stability Studies:

ATRA SLNs and Vitamin $D_3$-SLNs were stored in amber colored vials at 5±3° C. for 2 years the samples were withdrawn at 0, 3 and 6, 12 and 24 months, as per ICH guidelines. The formulations were found to retain stability over a long span of time.

13. Pharmacokinetic Studies:

In vivo pharmacokinetic studies were performed using male Wistar rats weighing 250-300 g. The protocol was duly approved by the Institutional Animal Ethics Committee (IAEC) of Panjab University, Chandigarh, India. The animals were divided into four groups (n=6). Group 1 was administered 2.5 Lacs International units (IU) subcutaneous retinoic acid and vitamin $D_3$ SLNs simultaneously, Group 2 was also simultaneously administered 2.5 Lacs IU free retinoic acid and vitamin $D_3$. Group 3 was administered simultaneously 1 Lac IU oral Retinoic acid and vitamin $D_3$ SLNs, Group 4 was administered simultaneously 1 Lac IU oral free Retinoic acid and vitamin $D_3$. The blood samples (0.5 mL) were withdrawn from sinus under clavicle and, collected into heparinized micro-centrifuge tubes (containing 20 mL of 1000 IU heparin/mL of blood) at 0.5 h, 1 h, 2 h, 4 h, 8 h, 12 h, 24 h, 48 h, 72 h, 96 h, 120 h, 144 h, 168 h. After each sampling, 1 mL of dextrose-normal saline was administered to prevent changes in the central compartment volume and electrolytes. Plasma was separated by centrifuging the blood samples at 4000 rpm for 10 min at 4° C. After centrifugation, the plasma obtained was stored at −20° C. until analysis.

14. Extraction Process of Plasma Samples:

500 microliter blank plasma was taken and into it added 20 microliter stock standard dilutions of different concentrations (0.01 mcg to 1 mcg) (vortex) and added 400 microliter of chilled ethanol (vortex) and to it was added 2 ml (n-Hexane:ethylacetate (90:10) (Vortex) and the same was kept at −20° C. for 5 min followed by Cold centrifuge at 5000 rpm for 5 min finally separating the upper layer carefully and drying the solution under rotavapour/nitrogen gas, after drying add 250 microliter of acetonitrile and inject the sample to HPLC/UPLC. The method was applied for extraction procedure for Pharmacokinetic samples after giving SLNs and free drugs of Retinoic acid and vitamin $D_3$ formulation to rats as oral/subcutaneous routes and sampling time points (0.5 h, 1 h, 2 h, 4 h, 8 h, 12 h, 24 h, 48 h, 72 h, 96 h, 120 h, 144 h, 168 h).

Example 2

Results
Analytical Method Development:

HPLC/UPLC method development for simultaneous determination of free drugs and drug incorporated in SLNs and applicability for pharmacokinetics.

Particle Size Analysis

The particle size is one of the characteristic features if the nanoparticle system is to be achieve bioavailability in plasma. The average size of the particles is also important with respect to the amount of drug entrapped and in vitro release pattern. Average particle size of the drug loaded nano-colloidal lipidic particles dispersions as obtained by Photon Correlation Spectroscopy was 157±4.0 nm and 147±6.0 nm for Retinoic acid and vitamin $D_3$ respectively. The small size obtained helped in achieving high concentrations of the drug in the plasma. The size and shape has been demonstrated to directly influence the uptake of nanoparticles into cells. For example, for nanoparticles larger than 100 nm the highest uptake was observed with rod shapes, followed by spheres, cylinders, and cubes.

Transmission Electron Microscopy (TEM)

The shape and size of Nano-colloidal lipidic particles can be depicted from TEM micrographs. TEM studies reveal the SLN particles rod in shape. Further, the particle size estimations were in conformity with those of the PCS technique. The particle size with TEM was observed to be 35.0±8.0 and 66±5.0 for Retinoic acid and vitamin $D_3$ respectively which confirmed the efficiency of the microemulsification method to be appropriate for preparation of small sized nano-colloidal lipidic particles.

Total Drug Content

The total drug content was estimated to be 92.50±2.10% and 91.2±2.1% for Retinoic acid and vitamin $D_3$ respectively. This indicates the efficiency of the method, for the preparation of SLN without encountering considerable losses during the formulation process.

Drug Entrapment

The drug entrapment efficiency of the developed nano-colloidal lipidic particles was found to be 84.60±3.20% and 84.65±2.7 respectively for Retinoic acid and Vitamin $D_3$, Use of lipid Compritol® 888 ATO (Glyceryl behenate) (Compritol 888 ATO®) has been reported to show high loading capacities of upto 86.5% in some earlier studies.

DSC

In DSC study, (FIG. 3) pure ATRA melting endotherm appeared at 187.34° C. corresponding to its melting point at

| S. No | Parameter | HPLC ALLIANCE SYSTEM e2695 with EMPOWER 2 SOFTWARE | | UPLC, AQUITY H-Class with EMPOWER 2 SOFTWARE | |
|---|---|---|---|---|---|
| | | Vitamin A | Vitamin D | Vitamin A | Vitamin D |
| 1 | Column | C18 | C18 | BEH C18 | BEH C18 |
| 2 | Mobile phase | ACN:MeOH:Water 90:8:2 | ACN:MeOH:Water 90:8:2 | ACN:MeOH:Water 90:8:2 | ACN:MeOH:Water 90:8:2 |
| 3 | Run time | 6 min | 6 min | 5 min | 5 min |
| 4 | Flow rate | 1.0 ml/min | 1.0 ml/min | 0.2 ml/min | 0.2 ml/min |
| 5 | Retention time | 2.5 min | 3.4 min | 0.98 min | 2.5 min |
| 6 | ($R^2$) | 0.999 | 0.999 | 0.999 | 0.999 |

Characterization: Particle Size, Total Drug Content and Entrapment Efficiency of Vitamin A and $D_3$ 180-189° C. and was associated with 84.03 J/g of enthalpy, while Compritol® 888 ATO showed a sharp peak at 73.6° C.

| Formulation | Particle size (nm) (n = 3) | Polydispersity Index (PI) | Zeta potential* (mV) | Total drug content (%) | Entrapment (%) (n = 3) |
|---|---|---|---|---|---|
| Retinoic acid | 157.0 ± 4.0 | 0.203 | −12.45 | 92.50 ± 2.10% | 84.60 ± 3.20% |
| Vitamin $D_3$ | 147.0 ± 6.0 | 0.230 | −2.61 | 91.2 ± 2.1 | 84.65 ± 2.7 | and an enthalpy of 108.3 J/g. Physical mixture, showed distinct endothermic peaks corresponding to both Compritol® 888 ATO and ATRA (lesser intensity because amount of ATRA present in the physical mixture was 10 times less than Compritol® 888 ATO). The ATRA-SLNs dispersion shows a very broad endotherm (which is a merger of several small peaks) starting from 63.81° C. to 102.99° C. with a low enthalpy of 13.43 J/g associated with the peak corresponding to the lipid at 74.10° C. Broadening of the peak indicates amorphous nature of ATRA-SLNs. In case of pure vitamin $D_3$ melting endotherm appeared at 90.74° C. corresponding to its melting point at 85-95° C. and was associated with 41.69 J/g of enthalpy, while Compritol® 888 ATO showed a sharp peak at 73.6° C. and an enthalpy of 108.3 J/g. Physical mixture, showed distinct endothermic peaks corresponding to both Compritol® 888 ATO and vitamin $D_3$ (lesser intensity because amount of vitamin $D_3$ present in the physical mixture was 10 times less than Compritol® 888 ATO). The Vitamin $D_3$-SLN dispersion shows a very broad endotherm (which is a merger of several small peaks) starting from 81.77° C. to 112.81° C. Broadening of the peak indicates amorphous nature of Vitamin $D_3$-SLNs. Further, the observation that enthalpy for the peak corresponding to the lipid is significantly lower than that of the pure lipid indicates the change in polymorphic state from the crystalline β form to the amorphous (α, β') form with more imperfections in the crystal lattice. Latter will comfortably incorporate the drug within the lipid molecules.

Powder X-Ray Diffraction (PXRD)

PXRD patterns of ATRA, Compritol® 888 ATO, lyophilized blank SLN (B-SLN), ATRA-SLN are shown in FIG. 4. PXRD pattern of ATRA exhibited sharp peaks at 2θ scattered angles 10.49, 14.64, 18.79, 23.43 and 29.51 which indicated its crystalline nature. PXRD pattern of Compritol® 888 ATO also show sharp peaks at 2θ scattered angles 21.16, 23.37, 23.52 and 35.76; again establishing its crystalline state.

However, no characteristic peaks in lyophilized B-SLN indicate the amorphous nature of lipid after transformation into SLNs. Typical pattern of peaks corresponding to those of free ATRA, were also found missing in the PXRD of lyophilized ATRA-SLNs sample, reconfirming the loss of crystallinity and a shift towards the amorphous state. PXRD patterns of Vitamin $D_3$, Compritol® 888 ATO, lyophilized blank SLN (B SLN), and Vitamin $D_3$-SLNs are shown in FIG. 5. PXRD pattern of Vitamin $D_3$ exhibited sharp peaks at 2θ scattered angles from 10-30, which indicated its crystalline nature. PXRD pattern of Compritol® 888 ATO also show sharp peaks at 2θ scattered angles 21.16, 23.37, 23.52 and 35.76; again establishing its crystalline state.

However, no characteristic peaks in lyophilized BSLN indicate the amorphous nature of lipid after transformation into SLNs. Typical pattern of peaks corresponding to those of free Vitamin $D_3$, were also found missing in the PXRD of lyophilized Vitamin $D_3$-SLNs sample, reconfirming the loss of crystallinity and a shift towards the amorphous state.

FTIR

The FTIR peaks (FIGS. 6 & 7) obtained with the developed formulation of ATRA-SLNs and vitamin $D_3$-SLNs reveal an inter-molecular stretching of the —OH groups (3400-3200 cm$^{-1}$) of, upon IR analysis, when compared with the peaks of the pure drug and the lipid. This may be regarded as direct indication of the formation of SLNs as the stretching could not be observed in case of ATRA, vitamin $D_3$ or Compritol® 888 ATO.

In Vitro Release

The in vitro release was found to be controlled and sustained for 7 days (See FIG. 1), when performed at 0.01 M pH 7.4 phosphate buffer. The initial release may be by diffusion from the shell of the nano-colloidal lipidic particles, while the subsequent phase of delayed release may be attributed to the fact that the Retinoic acid/Vitamin $D_3$ dispersed within the core is being released slowly from the solid matrices of lipid through diffusion and dissolution, also add to the sustained release for several days in phosphate buffer alone. For vitamin A, 79% release was obtained upto 7 days and 100% release was obtained for vitamin D after 7 days.

Stability Studies

ATRA-SLNs and Vitamin $D_3$-SLNs were stable for a period of 2 years, at 5±3° C., there was no significant change observed at the end of 2 years, in terms of assay, size and entrapment efficiency of both the vitamins.

Pharmacokinetic Studies

A major limiting factor to the systemic use of particulate delivery systems is the rapid clearance of carrier from the blood circulation by reticulo-endothelial system (RES). Various techniques such as suppression of RES (reducing particle size; 120-200 nm) and modification of surface characteristics of drug carriers by coating with hydrophilic agents/block copolymers have been attempted to reduce the RES uptake. The second approach has been shown to be highly effective in altering the bio-distribution pattern of colloidal drug carriers. Lower serum and tissue levels of Retinoic acid/Vitamin $D_3$ are observed in tuberculosis patients and a concentration of 1 μM of Retinoic acid/Vitamin $D_3$ was achieved to achieve its concentration for 4-7 days as controlled release to have protection against *mycobacterium tuberculosis*. Administration of vitamins (A and $D_3$) has been considered beneficial for the treatment of tuberculosis. Vitamin A (RA) acts synergistically with Vitamin $D_3$ to inhibit *mycobacterium* entry as well as survival within macrophages, possibly through rescue of phagosome maturation arrest. They thus provide a host protective mechanism rather than the *mycobacterium* directed mechanism shown by commonly used ATDs; since mycobacteria is highly resistant and can also shift strains, treatment with ATDs is less reliable while a host mediated pathway can be a gunshot treatment. Vitamin A and $D_3$ are water insoluble, light and air sensitive and hence these are incorporated into SLNs and administered by the subcutaneous/oral routes to achieve a controlled and sustained release so as to maintain their desired therapeutic concentration in plasma. Rate of absorption can be prolonged via giving these nanoparticles by subcutaneous route so that prolonged therapeutic concentration can be maintained in plasma for at least 4-7 days. Once *M. tuberculosis* is unable to establish itself on the macrophages it will die and will be flushed out from the system as Vitamin A and D are reported to down regulate its anchoring site on the macrophages.

While considerable emphasis has been placed herein on the particular features of this disclosure, it will be appreciated that various modifications can be made, and that many changes can be made in the preferred embodiments without departing from the principle of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

The plasma ATRA concentration versus time plots after oral and subcutaneous administration of ATRA-SLNS is shown in FIG. 8. At each time intervals, the plasma ATRA levels after oral and subcutaneous administration of the ATRA-SLNs were all significantly higher than that of the ATRA-S.

Besides, the plasma ATRA in the free drug group dropped to an undetectable level at 4 h after dosing, while the drug was still detectable until 48 h in the SLNs group. The in vivo process of both the formulations could be described by a single compartment model. The single dose subcutaneous pharmacokinetic parameters of the two formulations are shown in Table 1. The Cmax, AUC0-t and AUC0-∞ of the ATRA-SLNs reached 3.19 µg/ml, 14.98 µg·h/ml and 16.25 µg·h/ml respectively, while it was only 1.39 µg/ml, 2.82 µg·h/ml and 2.95 µg·h/ml, respectively, for the free drug. As being analyzed with sigmastat statistical software, all three parameters for the ATRA-SLNs were significantly higher than that of the free drug. Consequently, the subcutaneous bioavailability of ATRA-SLNs was 5.5 times higher than the ATRA-S, as calculated by AUC (t-∞).

In case of oral administration the Cmax, AUC0-t and AUCt-∞ of the ATRA-SLNs reached 1.04 µg/ml, 10.19 µg·h/ml and 14.79 µg·h/ml respectively, while it was only 0.151 µg/ml, 0.356 µg·h/ml and 0.713 µg·h/ml, respectively, for the free drug (Table 2). As being analyzed with sigmastat statistical software, all three parameters for the ATRA-SLNs were significantly higher than that of the free drug. Consequently, the oral bioavailability of ATRA-SLNs was 20.7 times higher than the ATRA-S, as calculated by AUC (t-∞).

As a BCS II drug, the solubility of ATRA is the main limitation for its oral bioavailability. Further, there was a significant reduction in Kel (8.5 times) in case of oral administration of ATRA-SLNs, which point towards a prolonged circulation time. Another, parameter depicting the longer plasma availability is the half life (t ½), which was increased by 10 times after incorporation into SLNs. Also in case of subcutaneous administration there was a significant reduction in Kel (10.5 times) and half life (t ½) increases by 14.4 times for ATRA-SLNs as compared to ATRA-S.

TABLE 1

Pharmacokinetic parameters of single dose subcutaneous injection of ATRA as free drug (ATRA-S) and upon loading into SLNs (ATRA-SLNs)

| Formulation | Subject | $C_{max}$ (ng/ml) | $T_{max(h)}$ | AUC (0-T) hr*ng/ml | AUC (T-∞) hr*ng/ml | CL (ml/hr/g) | Vd (ml/g) | Kel | T1/2 |
|---|---|---|---|---|---|---|---|---|---|
| ATRA-SLNs | 5 | 3190.54 | 0.70 | 14984.04 | 16254.00 | 16254 | 4268.92 | 0.07 | 13.71 |
| ATRA-S | 5 | 1396.98 | 0.50 | 2824.50 | 2945.55 | 1283.21 | 1763.47 | 0.74 | 0.95 |

TABLE 2

Pharmacokinetic parameters of single dose oral administration of ATRA as free drug (ATRA-S) and upon loading into SLNs (ATRA-SLNs)

| Formulation | Subject | Cmax (ng/ml) | Tmax (h) | AUC (0-T) hr*ng/ml) | AUC (T-∞) hr*ng/ml | CL (ml/hr/g) | Vd (ml/g) | Kel | T1/2 |
|---|---|---|---|---|---|---|---|---|---|
| ATRA-SLNs | 5 | 1045.72 | 1.50 | 10199.05 | 14797.67 | 103.43 | 7548.41 | 0.02 | 50.29 |
| ATRA-S | 5 | 151.27 | 0.90 | 356.55 | 713.51 | 218038 | 14198.25 | 0.17 | 4.84 |

The pharmacokinetic studies in rats revealed a significant improvement (p<0.05) in bioavailability after administration of 2.5 Lac International units (I.U) of subcutaneous vitamin $D_3$ loaded SLNs w.r.t. to free drug (vitamin $D_3$-S) of same dose. $C_{max}$ values for single subcutaneous vitamin $D_3$ loaded SLN dose (2.5 Lac I.U) was 322.54 ng/ml whereas free drug levels of same dose were below the level of quantification (less than 25 ng/ml). Some earlier studies report that $C_{max}$ of not more than 75 ng/ml in plasma was obtained even after administration of 4 repetitive doses of vitamin $D_3$. Significant levels i.e., 97 ng/ml in plasma could be maintained, even after 48 h post administration of vitamin $D_3$ loaded SLNs. Further clearance and $K_{el}$ of vitamin $D_3$ loaded SLNs was significantly low as compared to vitamin $D_3$-S, confirming the sustained effect of these nanoparticles upon subcutaneous administration (table 3).

The pharmacokinetic studies in rats also revealed a significant improvement (p<0.05) in bioavailability after administration of, 1 Lac IU of oral vitamin $D_3$ loaded SLNs w.r.t. to free drug (vitamin $D_3$-S) of same dose. $C_{max}$ values for single oral vitamin $D_3$ loaded SLN dose (1 Lac IU), was 374.79 ng/ml whereas free drug (same dose) were below the level of quantification (less than 25 ng/ml). Significant levels i.e., 111 ng/ml in plasma could be maintained, even after 48 h post administration of vitamin $D_3$ loaded SLNs. Further clearance and $K_{el}$ of oral vitamin $D_3$ loaded SLNs was significantly low as compared to free drug, vitamin $D_3$-S, respectively, confirming the sustained effect of these nanoparticles upon oral administration (table 4).

TABLE 3

Pharmacokinetic parameters of single dose subcutaneous injection of
Vitamin $D_3$ as free drug (Vitamin $D_3$-S) and upon loading into SLNs (Vitamin $D_3$-SLNs)

| Formulation | Subject | Cmax (ng/ml) | Tmax (h) | AUC (0-T) hr*ng/ml | AUC (T-∞) hr*ng/ml | CL (ml/hr/g) | Vd (ml/g) | Kel | T1/2 |
|---|---|---|---|---|---|---|---|---|---|
| Vitamin $D_3$-SLNs | 5 | 322.50 | 7.20 | 10110.57 | 14469.30 | 7.71 | 511.26 | 0.02 | 45.60 |
| Vitamin $D_3$-S | 5 | 0.0* | 0.0 | 0.0 | 0.0 | 0.0 | 0.0 | 0.0 | 0.0 |

*-Below level of detection

TABLE 4

Pharmacokinetic parameters of single dose oral administration of
Vitamin $D_3$ as free drug (Vitamin $D_3$-S) and upon loading into SLNs (Vitamin $D_3$-SLNs)

| Formulation | Subject | Cmax (ng/ml) | Tmax (h) | AUC (0-T) hr*ng/ml) | AUC (T-∞) hr*ng/ml | CL (ml/hr/g) | Vd (ml/g) | Kel | T1/2 |
|---|---|---|---|---|---|---|---|---|---|
| Vitamin $D_3$-SLNs | 5 | 374.79 | 6.4 | 9803.84 | 11316.42 | 4.38 | 199.75 | 0.03 | 29.61 |
| Vitamin D3-S | 5 | 0.0 | 0.0 | 0.0 | 0.0 | 0.0 | 0.0 | 0.0 | 0.0 |

*-Below level of detection

Example 3

Formulation 1

Glyceryl monostearate was melted at their melting point. Drug was added to the lipid phase. Lecithin and poloxamer dissolved in water were heated to the lipid melting point and added to the lipid phase. A clear and hot microemulsion was formed which was poured into ice-chilled water and homogenized for 30 minutes. Nanoparticles thus formed were characterized for particle size, total drug content, and entrapment efficiency. In-vitro release studies were performed with the developed dispersion.

| S No | Ingredients | mg/batch |
|---|---|---|
| 1. | Vitamin $D_3$/Retinoic acid | 30.00 |
| 2. | Glyceryl monostearte | 300.00 |
| 3. | Poloxamer 407 | 8.00 |
| 4. | Lecithin (4% solution of soya lecithin) | 0.1 ml |
| 5. | Water | 4.5 ml |

Formulation 2

Vitamin $D_3$/Retinoic acid and all other excipients were dispensed as per the formula. Briefly, Compritol was melted at its melting point. Drug was added to the lipid phase. Lecithin and Span 60 was added to hot aqueous phase maintained at the same temperature after which the two phases were mixed to form a clear microemulsion. Hot microemulsion thus formed was poured into ice-chilled water which was stirred mechanically for 120 minutes. Nanoparticles with a particle size 145 nm and PDI 0.106 were obtained.

| Components | mg/batch |
|---|---|
| Span 60 | 12.5 |
| Vitamin $D_3$/Retinoic acid | 10.0 |
| Compritol 888 ATO ® | 400 |
| Soya Lecithin, 4% sol in water | 0.8 ml |
| Water | 1.8 ml |

Formulation 3

Vitamin $D_3$/Retinoic acid and all other excipients were dispensed as per the formula. Drug was added to the melted lipid phase, and lecithin and poloxamer were added to the aqueous phase; lipid phase was added to the hot aqueous phase maintained on a magnetic stirrer at 150 rpm. A clear microemulsion thus obtained was stirred on a magnetic stirrer for 3 h. Nanoparticles with a particle size 108 nm and PDI 0.167 was obtained.

| Ingredients | mg/batch |
|---|---|
| Vitamin $D_3$/Retinoic acid | 20.00 |
| Poloxamer 188 | 20.00 |
| Palmitic acid | 60.00 |
| Poloxamer 407 | 8.00 |
| Lecithin | 3.5 |
| Water | 6 ml |

Formulation 4

Vitamin $D_3$/Retinoic acid and all other excipients were dispensed as per the formula. Glyceryl palmitostearte and poloxamer were melted at their melting point. Drug was added to the lipid phase and cosurfactant and surfactant were then added to the above mixture. A clear and hot microemulsion was formed which was poured into ice chilled water at mechanical stirrer for 3 h. Nanoparticles with a particle size (133 nm), with PDI 0.157 were obtained.

| Ingredients | mg/batch |
|---|---|
| Vitamin $D_3$/Retinoic acid | 30.00 |
| Glyceryl palmitostearte | 30.00 |
| Tween 20 | 4.00 |
| Poloxamer 407 | 18.00 |
| Sodium deoxy-taurocholate | 0.35 |
| Water | 10 ml |

Formulation 5

Vitamin $D_3$/Retinoic acid and all other excipients were dispensed as per the formula and stearic acid and poloxamer were melted at their melting point. Drug was added to the lipid phase. A clear and hot microemulsion was formed which was poured into ice-chilled water at mechanic stirrer for 3 h. Nanoparticles with particle size 178 nm, with PDI of 0.189 were obtained.

| Ingredients | Mg/batch |
| --- | --- |
| Vitamin $D_3$/Retinoic acid | 50.00 |
| Stearic acid | 80.00 |
| Soya lecithin H | 0.2 |
| Water | 20 ml |
| Tween 80 | 27 ml |

It has been able to entrap both the vitamins A and $D_3$ into SLNs, entrapment efficiency of 80% an 84% respectively for vitamin A and $D_3$ were achieved. Average Particle size for vitamin A was 134 nm and 189 nm for vitamin $D_3$ by Malvern particle size analyzer and TEM picture shows rod shaped particles. In vitro release study of SLNs formulation of vitamin A and $D_3$ was performed using 0.01 M Phospate Buffer pH 7.4 as the release media maintaining temperature at 37° C. and at 50 rpm.

Formulation 6

Vitamin $D_3$/Retinoic acid and all other excipients were dispensed as per the formula and glyceryl behenate was melted at its melting point. Tween, soy lecithin and water makes the aqueous phase at 80° C. Drug/Vitamin was added to the lipid phase. A clear and hot microemulsion was formed by mixing the lipid phase with the aqueous phase, microemulsion was poured into ice-chilled water at mechanic stirrer for 3 h. Nanoparticles with particle size 118 nm, with PDI of 0.189 were obtained.

| Ingredients | mg/batch |
| --- | --- |
| Vitamin $D_3$/Retinoic acid | 10.00 |
| Glyceryl behenate | 400.00 |
| Tween 80 | 2.5 ml |
| Soy lecithin | 0.8 ml of 4% aqueous solution |
| Water | 1.8 |

Advantages of the Invention

1. Enhanced and prolonged systemic bioavailability, resulting in maintenance of therapeutic concentrations for 2-7 days when administered orally or subcutaneous/i.v injections.
2. A spontaneous method of preparing highly concentrated dispersion of SLNs overcoming the need to concentrate the dilute dispersion resulting with other established methods.
3. Protection of drug/vitamins against oxidation and photodegradation due to incorporation into lipidic core.
4. Therapeutic use of combination of vitamin A and $D_3$ for the control of pulmonary and extrapulmonary TB including ocular, bone, cerebral, gastrointestinal tract tuberculosis,
5. The formulation of vitamin A can be extended for ocular use in the control of related macular degeneration (AMD), Diabetic retinopathy (DR), and hyperpigmentation (HP).
6. Vitamin A SLNs can be used as anticancer agent, and topically for the treatment of acne.
7. Vitamin $D_3$ SLNs can be used for control of osteoporosis.

The invention claimed is:

1. A process for preparing solid lipid nanoparticles containing at least one vitamin, said process comprising the following steps:
    i) preparing a lipid mix by melting one or more lipid selected from the group consisting of glycerides and fatty acids at a temperature at least equal to the melting point of said one or more lipid;
    ii) separately preparing an aqueous emulsifier mix by admixing at least one emulsifier and water followed by heating at a temperature at least equal to said melting point of said one or more lipid of step (i) and maintaining said temperature for a desired time interval;
    iii) adding at least one vitamin to the lipid mix produced in step (i) to obtain a solution or dispersion;
    iv) mixing the vitamin containing lipid mix in solution or dispersion from step (iii) with the aqueous emulsifier mix from step (ii) at said temperature to obtain a hot microemulsion;
    v) stirring the hot micro emulsion of step (iv) and simultaneously maintaining said temperature;
    vi) dispersing the hot microemulsion from step (v) in ice cold water maintained at a temperature ranging between 0° C. and 5° C. and at a 1:1 ratio;
    vii) continuously stirring/homogenizing the dispersion from step (vi) at least 5000 rpm for 1.5 to 3 hours; and
    viii) obtaining an aqueous dispersion of solid lipid nanoparticles having a particle size in the range of 5 nm to 500 nm and containing said at least one vitamin.

2. The process as claimed in claim 1, wherein in step (ii) the aqueous emulsifier mix comprises more than one emulsifier.

3. The process as claimed in claim 1, wherein the dispersing of the hot microemulsion from step (v) in cold water is followed by continuously stirring/homogenizing the dispersion at 5,000 to 7,000 rpm for up to 2 hours.

4. The process as claimed in claim 1, wherein the one or more lipids in step (1) are glycerides selected from the group consisting of mono-glycerides, di-glycerides and tri-glycerides.

5. The process claimed in claim 1, wherein the one or more lipids in step (i) are glycerides selected from the group consisting of glyceryl behenate (Compritol 888ATO®), tricaprin, trilaurin, trimyristin, tripalmitin, tristearin, 1,2-dioctanoyl-sn-glycerol, 1,2-didecanoyl-sn-glycerol, 1,2-dilauroyl-sn-glycerol, 1,2-dimyristoyl-sn-glycerol, 1,2-dipalmitoyl-sn-glycerol, 1-palmitoyl-2-oleoyl-sn-glycerol, 1-stearoyl-2-linoleoyl-sn-glycerol, 1-stearoyl-2-arachidonoyl-sn-glycerol, 1-stearoyl-2-docosahexaenoyl-sn-glycerol, 1-oleoyl-2-acetyl-sn-glycerol, 1,2-di-O-phytanyl-sn-glycerol, 1,2-dipalmitoyl ethylene glycol, 1-2-dioleoyl ethylene glycol, glyceryl monostearate, behenoyl polyoxyl-8 glycerides, glyceryl palmitostearate, 1-O-hexadecyl-sn-glycerol, 1-O-hexadecyl-2-acetyl-sn-glycerol, 1-O-hexadecyl-2-O-methyl-sn-glycerol, 1,2-diacyl-3-O-(α-D-glucopyranosyl)-sn-glycerol, stearoyl macrogol-32 glycerides, stearoyl polyoxyl-32 glycerides, lauroyl macrogol-32 glycerides, lauroyl polyoxyl-32 glycerides, lauroyl macrogol-6 glycerides, lauroyl polyoxyl-6 glycerides, oleoyl macrogol-6 glycerides, oleoyl polyoxyl-6 glycerides, linoleoyl macrogol-6 glycerides, polyglyceryl-3 dioleate, glyceryl monolinoleate, glyceryl monolinoleate, glycerol monooleates, diethylene glycol monoethyl ether, glyceryl dibehenate, glycerol distearate, glyceryl distearate, glyceryl dipalmitostearate and linoleoyl polyoxyl-6 glyceride.

6. The process as claimed in claim 1, wherein the one or more lipids in step (i) are fatty acids selected from the group consisting of saturated $C_4$-$C_{28}$ fatty acids and unsaturated $C_4$-$C_{28}$ fatty acids.

7. The process as claimed in claim 1, wherein the at least one emulsifier in step (ii) is selected from the group consisting of anionic emulsifiers, cationic emulsifiers, non ionic emulsifiers or zwitterionic emulsifiers.

8. The process as claimed in claim 1, wherein the at least one emulsifier in step (ii) is selected from the group consisting of soya lecithin, egg lecithin, phosphatidylcholine; ethylene oxide copolymers, propylene oxide copolymers, poloxamers, sorbitan ethylene oxide/propylene oxide copolymers, polysorbate 20, polysorbate 60, polysorbate 80, sorbitan esters, span 20, span 40, span 60, span 80, alkyllaryl polyether alcohol polymers, tyloxapol, bile salts, cholate, glycocholate, taurocholate, taurodeoxycholate, gemini surfactants and alcohols.

9. The process as claimed in claim 1, wherein the at least one vitamin in step (iii) is selected from the group consisting of fat soluble vitamin such as Vitamin A, D, E and K.

10. The process as claimed in claim 9, wherein the at least one vitamin in step (iii) is selected from Vitamin A, Vitamin D or an alternate form or derivative thereof.

11. The process as claimed in claim 10, wherein the vitamin A is selected from the group consisting of retinoic acid, vitamin A retinol, retinal, and carotenoids such as beta carotene or derivatives or metabolites thereof.

12. The process as claimed in claim 10, wherein the vitamin is D is selected from the group consisting of Vitamin $D_3$ or Vitamin $D_2$ or its derivatives or other metabolites thereof.

13. The process as claimed in claim 10, wherein the vitamin is retinoic acid or Vitamin $D_3$.

14. The process as claimed in claim 1, wherein the making of the aqueous emulsifier mix in step (ii) includes mixing two emulsifiers or surfactants such as Polysorbate 80 and Soya Lecithin.

15. Solid lipid nanoparticles containing at least one vitamin prepared by the process as claimed in claim 1, said solid lipid nanoparticles comprising:
    i) at least one lipid selected from the group consisting of glycerides and fatty acids;
    ii) at least one vitamin, selected from the fat soluble vitamins such as Vitamin A, D, E and K; and
    iii) at least one emulsifier.

16. The solid lipid nanoparticles containing at least one vitamin claimed in claim 15, wherein the vitamin is selected from Vitamin A or Vitamin D or an alternate form or a derivative thereof, or wherein the glyceride is selected from the group consisting of glyceryl behenate, tricaprin, trilaurin, trimyristin, tripalmitin, tristearin, 1,2-dioctanoyl-sn-glycerol, 1,2-didecanoyl-sn-glycerol, 1,2-dilauroyl-sn-glycerol, 1,2-dimyristoyl-sn-glycerol, dipalmitoyl-sn-glycerol, 1-palmitoyl-2-oleoyl-sn-glycerol, 1-stearoyl-2-linoleoyl-sn-glycerol, 1-stearoyl-2-arachidonoyl-sn-glycerol, 1-stearoyl-2-docosahexaenoyl-sn-glycerol, 1-oleoyl-2-acetyl-sn-glycerol, 1,2-di-O-phytanyl-sn-glycerol, 1,2-dipalmitoyl ethylene glycol, 1-2-dioleoyl ethylene glycol, glyceryl monostearate, behenoyl polyoxyl-8 glycerides, glyceryl palmitostearate, 1-O-hexadecyl-sn-glycerol, 1-O-hexadecyl-2-acetyl-sn-glycerol, 1-O-hexadecyl-2-O-methyl-sn-glycerol, 1,2-diacyl-3-O-(a-D-glucopyranosyl)-sn-glycerol, stearoyl macrogol-glycerides, stearoyl polyoxyl-32 glycerides, lauroyl macrogol-32 glycerides, lauroyl polyoxyl-32 glycerides, lauroyl macrogol-6 glycerides, lauroyl polyoxyl-6 glycerides, oleoyl macrogol-6 glycerides, oleoyl polyoxyl-6 glycerides, linoleoyl macrogol-6 glycerides, polyglyceryl-3 dioleate, glycerol monolinoleate, glyceryl monolinoleate, glycerol monooleates, diethylene glycol monoethyl ether, glyceryl dibehenate, glycerol distearate, glyceryl distearate, glyceryl dipalmitostearate and linoleoyl polyoxyl-6 glyceride, preferably, glyceryl behenate, and wherein the emulsifier is selected from the group consisting of soy lecithin, egg lecithin, phosphatidylcholine; ethylene oxide copolymers, propylene oxide copolymers, poloxamers, sorbitan ethylene oxide/propylene oxide copolymers, polysorbate 20, polysorbate 60, polysorbate 80, sorbitan esters, span 20, span 40, span 60, span 80, alkyllaryl polyether alcohol polymers, tyloxapol, bile salts, cholate, glycocholate, taurocholate, taurodeoxycholate, gemini surfactants and alcohols.

17. The solid lipid nanoparticles containing at least one vitamin claimed in claim 15, wherein the solid lipid nanoparticles have the following structure:
    a. an innermost lipid core consisting of a solid lipid encapsulating the vitamin in its solid matrix;
    b. a shell with an outer layer consisting of a mixture of surfactants; and
    c. a nanoparticulate structure or an assembly thereof, surrounded by the aqueous solution of unused surfactant and unentrapped vitamin.

18. The solid lipid nanoparticles containing at least one vitamin claimed in claim 15, wherein the amount (content) of vitamin is in the range of 5% to 40% with respect to the mass of the lipid, or wherein the drug entrapment is in the range of 60% to 100%.

19. The solid lipid nanoparticles containing at least one vitamin claimed in claim 15, wherein the particle size of the solid lipid nanoparticles ranges between 5 to 500 nm.

20. A concentrated nano-formulation formed by the process as claimed in claim 1, wherein the ratio of microemulsion to water ranges between 1:1 to 1:4.9.

* * * * *